June 25, 1963 C. E. SCHMALZ ETAL Plant Pat. 2,268
ROSE PLANT
Filed July 9, 1962
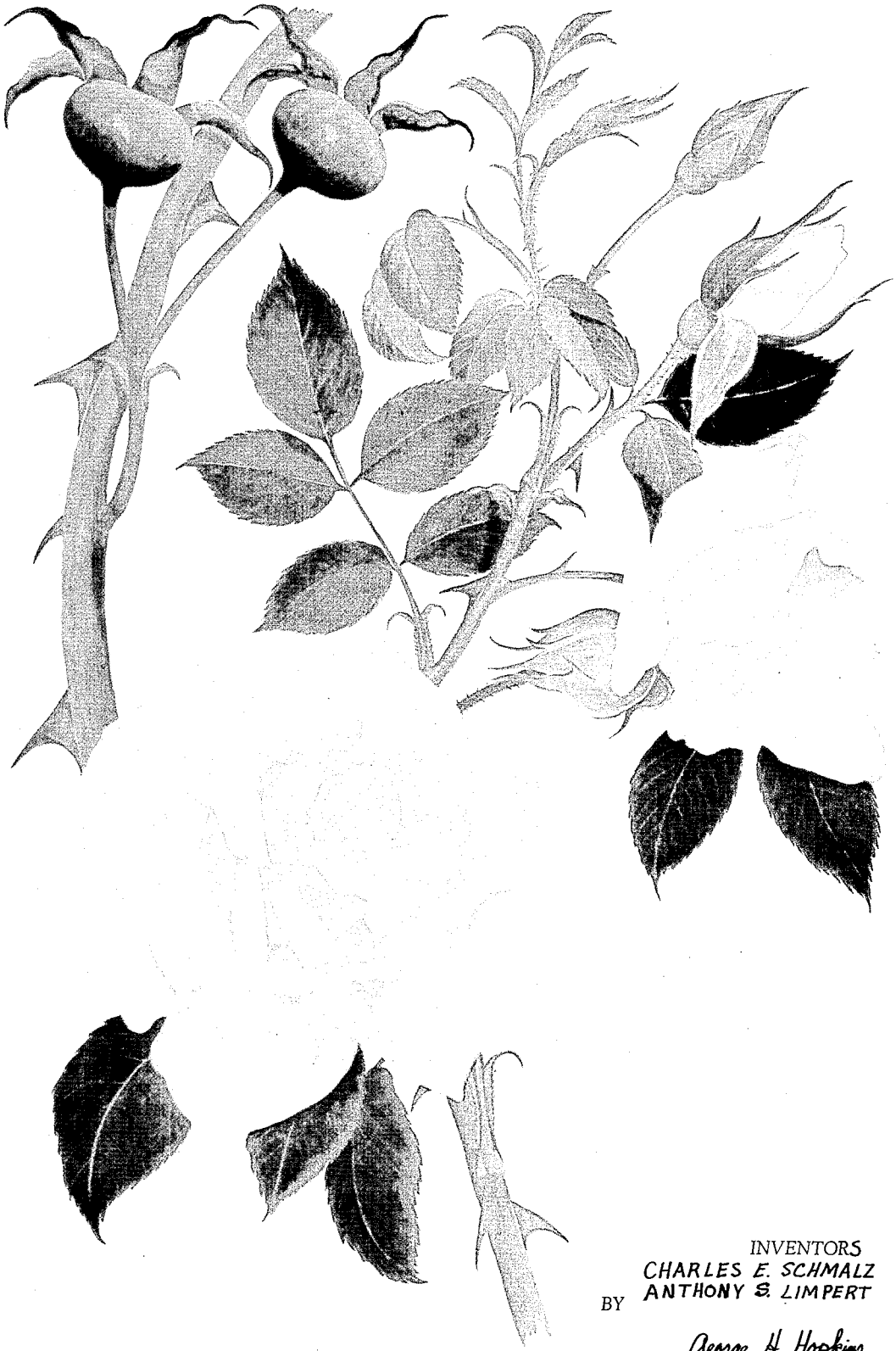
INVENTORS
CHARLES E. SCHMALZ
ANTHONY S. LIMPERT
BY George H. Hopkins
ATTORNEY United States Patent Office Plant Pat. 2,268
Patented June 25, 1963

2,268
ROSE PLANT

Charles E. Schmalz, Greece, and Anthony S. Limpert, Rochester, N.Y.; said Limpert assignor to said Schmalz Filed July 9, 1962, Ser. No. 208,656
1 Claim. (Cl. Plt.—2)

This invention pertains to a new and distinct variety of rose plant of the climber class, which is a cultivated sport derived from the variety "Doubloons" (Plant Patent No. 152).

The rose plant of this invention has a number of outstanding and distinctive features. It has many of the characteristics of a typical rose plant of the hybrid tea class and yet it is a climber. Compared to a typical climber, it produces long, upright stems, large flowers, well shaped buds and clean shiny foliage. The petals when the buds first open recurve and retain this form to maturity. The blooms have good keeping qualities, have a pleasing, long lasting fragrance and a remarkable color habit. The blooming period of the rose plant is widespread, from early to about midway in the growing season at Rochester, New York. However, during this period the plant blooms but once with the flowers being borne singly with occasional side buds. On the other hand, the rose plant of the invention propagates well and has better than average mildew resistance. These principal characteristics together are unique in the climber class and distinguish the rose plant of this invention from all other varieties of which we are aware.

Asexual reproduction of our new variety by budding, performed at Rochester, New York, shows that these characteristics and distinctions come true to form and are established and transmitted through succeeding propagations.

The accompanying drawing shows typical specimens of the vegetative growth and flowers of our new variety in different stages of development and as depicted in color as nearly true as reasonably possible in a color illustration of this character.

A detailed description of our new variety follows. The color terminology employed therein is in accordance with Ridgway's Color Standards and Nomenclature, except where general color terms of ordinary dictionary significance are used. This description is based on observations made of typical specimens grown outdoors at Rochester, New York.

Type: Pillar; outdoor; cultivated sport; for cut flowers and for garden decoration.

Class: Climber.

Breeding: Cultivated sport from "Doubloons" (Plant Patent No. 152).

Propagation: Holds its distinguishing characteristics through succeeding propagations by budding.

*Flower*

Flowers borne: Mostly singly on strong, long stems; occasional side buds.

Quantity of bloom: Abundant, outdoors.

Continuity: Blooms once during period from early to about midway in growing season.

Fragrance: Moderate. Nature—similar to freshly ground pepper.

Bud:

*Peduncle.*—Long; from slender to medium slender; erect; prickly aspect. Color when new—near Mineral Red, Plate XXVII. Color at maturity—Pea Green, Plate XLVII.

*Before calyx breaks.*—Size—large. Form—medium length; pointed; ovoid.

*As calyx breaks.*—Color—at base: Turtle Green, Plate XXXII, suffused with Mineral Red, Plate XXVII; at tip: Deep Dull Yellow-Green (1), Plate XXXII.

*Sepals.*—Slightly branched; curl back as calyx breaks; aspect—smooth outside, hairy inside.

*As first petal opens.*—Size—large (⅞ inch wide by 1⅛ inch long). Form—pointed; ovoid. Color—outside: Eosine Pink, Plate I, blending to Pale Yellow-Orange, Plate III; inside: Light Orange-Yellow, Plate III.

*Opening.*—Opens up well. Is not retarded by cold, hot, wet or dry weather.

Bloom:

*Size (when fully open).*—Medium large; from 3½ to about 4 inches.

*Petalage.*—Double; about 30 petals plus 2–6 petaloids; arranged irregularly.

*Stem.*—Long; average of 14–16 inches; strong.

*Form.*—High centered at first with petals recurving and retaining recurved form to maturity; full but open center which is hidden until bloom pancakes.

*Petals.* — Thick; inside — satiny; outside — satiny; shape—scalloped; informal.

*Color* (observations made on freshly cut blooms during the middle part of June at Rochester, New York).—One-third open: outer petals, outside surface—at base Lemon Chrome, Plate IV, grading to Maize Yellow, Plate IV, at tip; inner petals, outside surface—at base Lemon Chrome, Plate IV, blending to Maize Yellow, Plate IV, at tip. Fully open: same except that tips of recurved petals are 1''' Red, Plate XXXIX.

*General color effect.*—One-third open—pink; fully open—light pink when blossom goes to maturity on plant outdoors and approximately Shrimp Pink, Plate I, when blossom on cut stem goes to maturity indoors.

*Behavior.*—Petals drop off cleanly; not particularly affected by cold, hot, wet or dry weather.

*Flower longevity.*—Uncut—3 days in June; cut blooms grown outdoors and kept at room temperatures indoors—4–5 days in June.

*Reproductive Organs*

Stamens: Many; arranged regularly around pistils.

Filaments: Most with anthers; variable length with longer ones on outside and shorter ones towards center. Color—Primuline Yellow, Plate XVI.

Anthers: Large; all open approximately at once. Color—Primuline Yellow, Plate XVI.

Pollen: Moderate abundance. Color—Primuline Yellow, Plate XVI.

Pistils: Medium number.

Styles: Even; long; thin; bunched. Color—Amber Yellow, Plate XVI.

Stigma: Color—Naphthalene Yellow, Plate XVI.

Ovaries: All enclosed in calyx.

*Fruit*

Form: Subglobose—resembles Gallica versicolor but with slight neck at calyx end.

Aspect: Smooth.

Color: At maturity—generally red.

Sepals: Permanent; curled. Color—yellow.

*Plant*

Foliage:

*Leaves.*—Compound of 5 leaflets; abundant; medium; upper side—leathery; under side—smooth.

*Leaflets.*—Shape—roundly oval with apex acute; base—round; edge—small, double serration.

*Color.*—Young—upper surface, Deep Dull Yellow-Green (1), Plate XXXII, suffused with Mineral Red, Plate XXVII; under surface, same. Mature—upper surface, Deep Dull Yellow Green (1), Plate XXXII; under surface, same.

*Leaf stem.*—Average size. Upper side—smooth. Under side—prickles.

*Stipules.*—Variable length. Narrow with short points turning out at an angle of about 45°.

*Disease resistance.*—Better than average resistance to mildew, compared, for example, to the variety Summer Snow grown under comparable cultural conditions at Rochester, New York.

Growth:

*Habit.*—Upright; tall; compact with flowers occurring usually singly on long cutting stems.

*Growth.*—Very vigorous.

*Canes.*—Heavy.

*Main stems.*—Dull; color—Malachite Green, Plate XXXII. Thorns — many; long; hooked downwardly; broad base; color when young—Tyrian Red, Plate XII. Prickles—few; color—reddish green. Hairs—none.

*Branches.*—Dull. Color—Malachite Green, Plate XXXII. Thorns—average number; long; hooked downwardly; broad base; color when young—Tyrian Red, Plate XII. Prickles—few; color—reddish green. Hairs—none.

*New shoots.*—Dull. Color—Amaranth Purple, Plate XII. Thorns — average number; long; hooked downwardly; broad base; color—Tyrian Red, Plate XII. Prickles — few; color — reddish green. Hairs—none.

We claim:

A new and distinct variety of rose plant, substantially as herein shown and described.

No references cited.